United States Patent [19]

Vassel

[11] Patent Number: 5,319,987
[45] Date of Patent: Jun. 14, 1994

[54] SAMPLE COLLECTING APPARATUS

[76] Inventor: Jeffrey Vassel, Rte. 2, Box 188, Minter City, Miss. 38944

[21] Appl. No.: 870,575

[22] Filed: Apr. 17, 1992

[51] Int. Cl.$^5$ .................................. G01N 1/20
[52] U.S. Cl. ..................... 73/863.710; 73/863.51; 73/863.81
[58] Field of Search ............ 73/863.51, 863.52, 863.53, 73/863.54, 863.71, 863.81, 863.82, 863.85, 864

[56] References Cited

U.S. PATENT DOCUMENTS

| | | | |
|---|---|---|---|
| 1,966,712 | 7/1934 | Fisher et al. | 73/863.54 |
| 2,370,260 | 2/1945 | Robison | 73/863.86 |
| 2,683,373 | 7/1954 | Gallup et al. | 73/863.53 |
| 2,746,297 | 5/1956 | Martin | 73/421 |
| 3,034,360 | 5/1962 | Hampl | 73/864.74 |
| 3,066,539 | 12/1962 | Coker et al. | 73/863.81 |
| 3,076,341 | 2/1963 | Murray et al. | 73/863.53 |
| 3,949,614 | 4/1976 | Abonnenc | 73/863.83 |
| 4,218,920 | 8/1980 | John, Jr. | 73/863.52 |
| 4,294,124 | 10/1981 | Kalwaitis | 73/863.85 |
| 4,409,853 | 10/1983 | Chase et al. | 73/863 |
| 4,625,570 | 12/1986 | Witherspoon et al. | 73/863.81 |
| 4,635,470 | 1/1987 | Skallen et al. | 73/63 |
| 4,708,011 | 11/1987 | Rautakorpi et al. | 73/63 |
| 4,771,642 | 9/1988 | Parth et al. | 73/863.54 |

FOREIGN PATENT DOCUMENTS 0005897 4/1964 Japan .................. 73/863.53

*Primary Examiner*—Tom Noland
*Assistant Examiner*—Daniel S. Larkin
*Attorney, Agent, or Firm*—John R. Flanagan

[57] ABSTRACT

A sample collecting apparatus includes a housing, sample container, and handle. The housing is open at front and rear opposite ends and has a semi-cylindrical portion defining a bottom discharge opening located between its opposite ends. The container is mounted within the housing for sliding movement along and rotational movement about a common longitudinal axis of the housing and container. The container has a semi-cylindrical middle portion defined between front and rear cylindrical end portions. The container has a pair of spaced circular walls disposed at opposite ends of the semi-cylindrical middle portion defining a semi-cylindrical sample holding cavity. The handle is connected to the front end portion of the container and extends axially forwardly therefrom through the interior of the housing and from the open front end thereof. The handle is gripped to slidably move the container along and rotate the container about the common longitudinal. The container is slidable between a rearward position and a forward position. At the rearward position, the sample holding cavity of the container is disposed beyond the rear end of the housing in an upright orientation for receiving a sample. After reaching the forward position aligned with the bottom discharge opening of the housing, the container can be rotated about the longitudinal axis to dispose the sample holding cavity in an inverted position for discharging the sample.

16 Claims, 2 Drawing Sheets

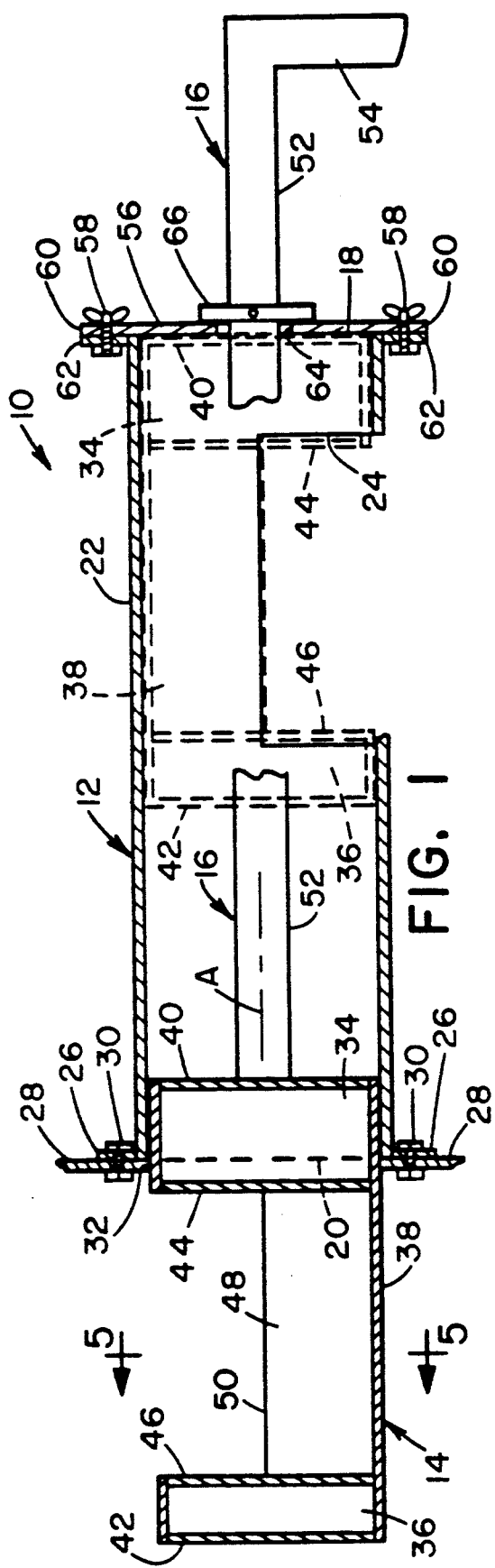
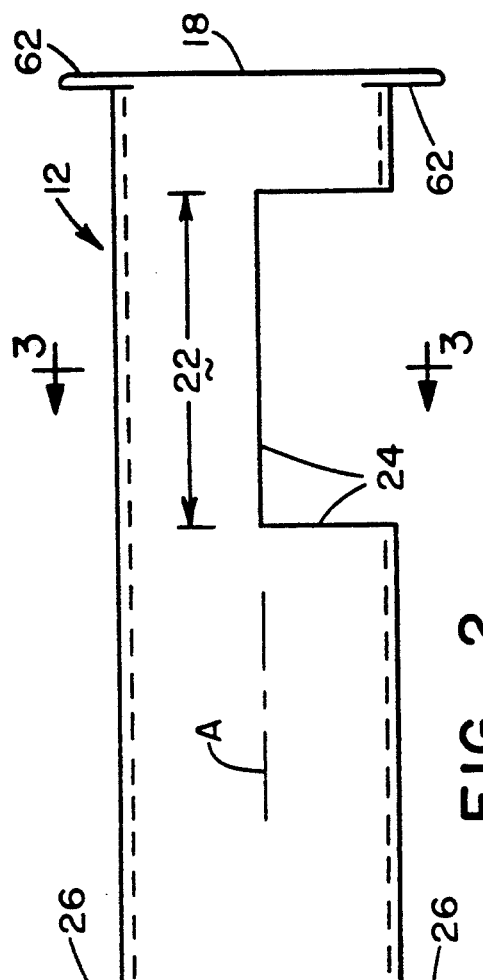
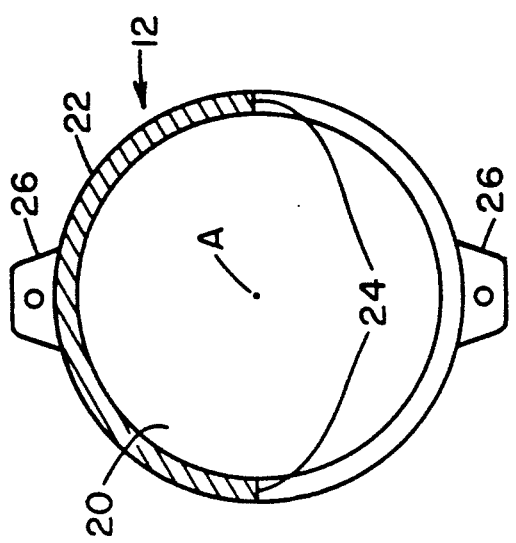

SAMPLE COLLECTING APPARATUS

BACKGROUND OF THE INVENTION

1. Field of the Invention

The present invention generally relates to sampling techniques and, more particularly, is concerned with a sample collecting apparatus particularly suited for use in the paper making industry.

2. Description of the Prior Art

A growing number of new paper making plants employ a thermo-mechanical pulping process as opposed to a chemical pulping process employed by old plants. One significant advantage of the thermo-mechanical pulping process is that it does not, to any significant degree, emit noxious odors as does the chemical pulping process.

In the thermo-mechanical pulping process, a suitable feed stock, such as wood chips, is mechanically processed into pulp fibers having the desired length. The wood chips are initially transferred into a primary refiner where they are ground into relatively long pulp fibers by grinding components having coarse teeth. The pulp fibers are next tranferred from the primary refiner to a secondary refiner where they are ground into pulp fibers of relatively short lengths by grinding components having fine teeth. After the secondary refiner, the pulp goes through a screening process wherein a screen passes pulp fibers of lengths below a maximum allowable length and rejects over-length pulp fibers. The rejected pulp fibers are transferred to a reject refiner where they are ground to reduce their lengths to below the maximum allowed.

During processing of the rejected pulp fibers in the reject refiner under atmospheric pressure and at temperatures ranging from 160° to 180° F., samples have to be taken periodically from a stream of ground pulp fibers falling through a chute under the influence of gravity. These samples are then taken to a laboratory where they are subjected to appropriate quality control tests.

Heretofore, in order to take a sample, a port hole in the wall of the chute has had to be unplugged and an elongated probe inserted through the hole into the pulp stream. This current procedure has certain problems. At unplugging of the port hole, frequently some of the pulp ejects from the chute through the port hole, thereby exposing the technician to hazardous contact with pulp at scalding temperatures and causing splattering and contaminating of the surrounding area with the ejected pulp.

Consequently, a need exists for improvements in the way samples are taken so as to avoid the problems of the current sampling procedure.

SUMMARY OF THE INVENTION

The present invention provides a sample collecting apparatus designed to overcome existing problems and satisfy the aforementioned need. The sample collecting apparatus allows a technician to quickly and safely obtain a sample through a wall of an enclosure containing the material being sampled while avoiding the possibility of material being ejected or splashed on the technician and the surrounding area outside of the housing.

Accordingly, the present invention is directed to a sample collecting apparatus comprising: (a) an elongated tubular housing having spaced front and rear opposite ends and a middle portion defining an opening in the housing located between and spaced from the opposite ends, at least the rear end of the housing being open; (b) a tubular sample container mounted within the housing for sliding movement along and rotational movement about a longitudinal axis extending between the opposite ends of the housing, the container having spaced front and rear end portions and a middle portion located between and spaced from the front and rear end portions, the container also having a pair of spaced walls disposed at opposite ends of the middle portion defining a sample holding cavity having an opening; and (c) means for slidably and rotatably moving the container along and about the longitudinal axis between a rearward position in which the cavity of the container in a first orientation extends beyond the open rear end of the housing for receiving a sample and the forward end portion of the container substantially fills the open rear end of the housing and a forward position in which the cavity of the container in a second orientation aligns with the opening of the housing for discharging the sample and the rearward end portion of the container substantially fills the open rear end of the housing.

Further, the sample collecting apparatus includes means mounted at the front end of the housing for engaging the front end portion of the container and stopping sliding movement of the container at the forward position in the housing. The front end of the housing is open. The engaging and stopping means is a removable stop plate attached across the open front end of the housing and having a slot defined therein. The means for slidably and rotatably moving the container is an elongated arm connected to the front end portion of the container. The arm extends forwardly through the housing and through the slot in the stop plate attached to the front end of the housing and extends from the housing to where the arm has a transverse handle that can be gripped to slidably move the container along and rotate the container about the longitudinal axis. A blocking element in the form of an annular collar is mounted on the arm adjacent to and spaced from the handle for engaging the stop plate attached across the open front end of the housing to stop sliding movement of the sample container at the rearward position.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a longitudinal sectional view of a sample collecting apparatus of the present invention.

FIG. 2 is a side elevational view of a tubular housing of the sample collecting apparatus of FIG. 1.

FIG. 3 is an enlarged cross-sectional view of the tubular housing taken along line 3—3 of FIG. 2.

DETAILED DESCRIPTION OF THE INVENTION

Figure 4:
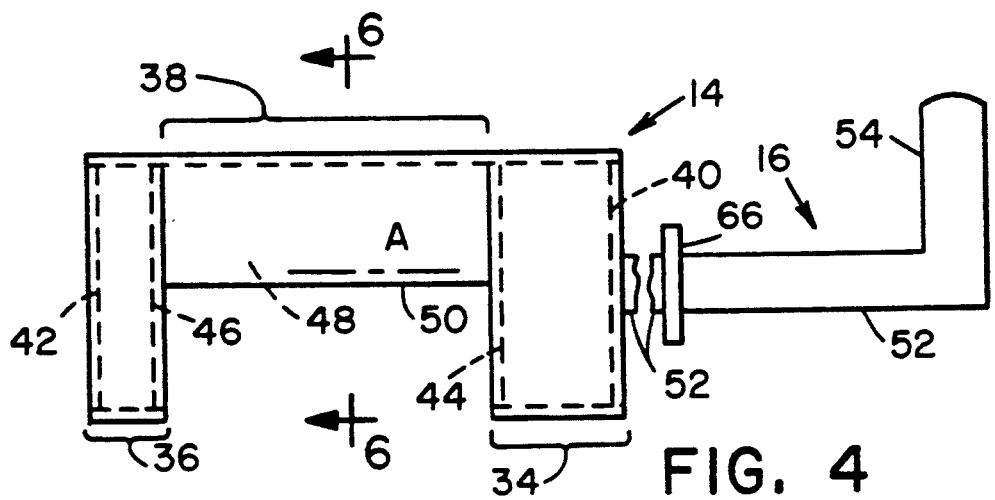
FIG. 4 is a side elevational view of a sample container of the sample collecting apparatus of FIG. 1, the sample container being shown in an inverted position.
Figure 5:
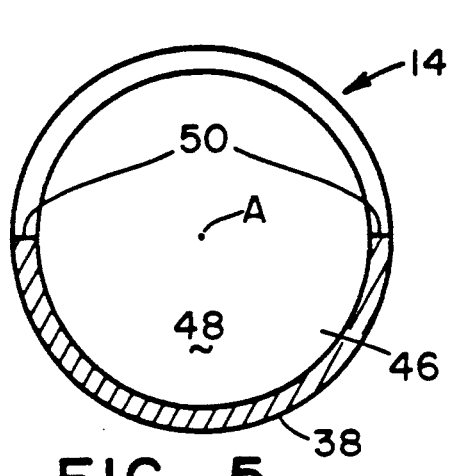
FIG. 5 is an enlarged cross-sectional view of the sample container taken along line 5—5 of FIG. 1, showing the sample container in an upright position.
Figure 6:
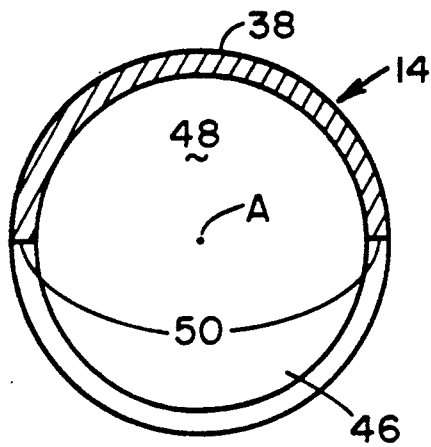
FIG. 6 is an enlarged cross-sectional view of the sample container taken along line 6—6 of FIG. 4, showing the sample container in the inverted position.

Referring to the drawings and particularly to FIG. 1, there is illustrated a sample collecting apparatus, generally designated 10, of the present invention. The sample collecting apparatus 10 is particularly suited for use in the paper making industry for sampling pulp being processed under atmospheric pressure conditions. However, the use of the apparatus in other sampling applications is equally possible. Basically, the sample collecting apparatus 10 includes a tubular housing 12, a sample container 14, and a gripping means 16.

Referring to FIGS. 1–3, the tubular housing 12 of the apparatus 10 is in the form of an elongated cylindrical sleeve 12 having a hollow interior, a pair of spaced front and rear opposite open ends 18, 20 and a semi-cylindrical middle portion 22 defining a bottom opening 24 in the tubular housing 12. The middle portion 22 and bottom opening 24 of the tubular housing 12 are located between and spaced from the front and rear open ends 18, 20 thereof. For reasons that will become clear later, the middle portion 22 and bottom opening 24 are located nearer to the front open end 18 than to the rear open end 20 of the tubular housing 12.

The tubular housing 12 has a suitable bracket 26 attached about the rear open end 20 of the tubular housing 12 for mounting the tubular housing 12 to an exterior side of a wall 28 of an enclosure containing a material to be sampled. As seen in FIG. 1, the tubular housing 12 is secured on the wall 28 by fasteners 30 with its open rear end 20 in alignment with a hole 32 formed through the wall 28 for gaining access to the interior side of the wall 28. In a preferred application of the sample collecting apparatus 10, the enclosure is a chute through which a stream of ground pulp is falling under the influence of gravity and at atmospheric pressure and at temperatures ranging from 160° to 180° F.

Referring to FIGS. 1 and 4–6, the sample container 14 of the apparatus 10 is in the form of an elongated cylindrical body 14 having a hollow interior and a pair of spaced front and rear cylindrical end portions 34, 36 and a middle semi-cylindrical portion 38 located between the front and rear end portions 34, 36. The sample container 14 has a pair of circular outer end walls 40, 42 attached on the opposite ends of the sample container 14 (which also are the outer ends of the front and rear end portions 34, 36) and a pair of circular inner end walls 44, 46 attached at the opposite ends of the semi-cylindrical portion 38 (which also are the inner ends of the front and rear end portions 34, 36). The semi-cylindrical portion 38 and the inner end walls 44, 46 together define a semi-cylindrical sample holding cavity 48 having an opening 50.

The sample container 14 of the apparatus 10 has a diameter slightly less than the diameter of the tubular housing 12, adapting the container 14 to mount within the hollow interior of the tubular housing 12 for sliding movement along and rotational movement about a common longitudinal axis A of the tubular housing 12 and sample container 14. The sample container 14 is slidable along a longitudinal axis A between a rearward position, as shown in solid line form in FIG. 1, and a forward position, as shown in dashed line form in FIG. 1. Also, the sample container 14 is rotatable about the longitudinal axis A between first and second orientations which are preferably angularly displaced approximately 180° from one another.

At the rearward position shown in solid line form in FIG. 1, the sample holding cavity 48 of the sample container 14 extends beyond the rear open end 20 of the tubular housing 12 in the first, preferably upright, orientation for receiving a sample. Also, at the rearward position, the front end portion 34 of the sample container 14 substantially fills the rear open end 20 of the tubular housing 12. Thus, during collecting of a sample of material in the cavity 48 of the container 14 extending from the rear open end 20 of the tubular housing 12, the rear open end 20 is blocked and material is prevented from ejecting through the hollow interior of the tubular housing 12.

At the forward position shown in dashed line form in FIG. 1 in which the sample holding cavity 48 of the sample container 14 is aligned with the bottom discharge opening 24 of the tubular housing 12, the container 14 will be rotated about the longitudinal axis A to the second, preferably inverted, orientation, to dispose the opening 50 of the sample holding cavity 48 in direct communication with the bottom opening 24 of the tubular housing 12 for discharging the sample from the sample container cavity 48 through the tubular housing opening 24. Also, at the forward position, the rear end portion 36 of the sample container 14 substantially blocks any path through the interior of the tubular housing 12 between the bottom opening 24 and the rear open end 20 of the tubular housing 12. Thus, during moving of the container 14 from the rearward to forward position and discharging of the sample of material held in the cavity 48 of the container 14 through the bottom opening 24 of the tubular housing 12, the path is blocked through the interior of the tubular housing 12 between the bottom opening 24 and the rear open end 20 of the tubular housing 12 such that material is prevented from ejecting through the hollow interior of the tubular housing 12.

Referring to FIGS. 1 and 4, the gripping means 16 of the apparatus 10 for slidably and rotatably moving the sample container 14 is an elongated arm 52 connected to the front end portion 34 of the sample container 14 and extending forwardly therefrom through the hollow interior of the tubular housing 12 and through the front open end 18 of the tubular housing 12. The portion of the arm 52 extending from the tubular housing 12 has a transverse handle 54 on its forward end. The handle 54 is gripped to slidably move the sample container 14 along and rotate it about the longitudinal axis A.

Figure 7:
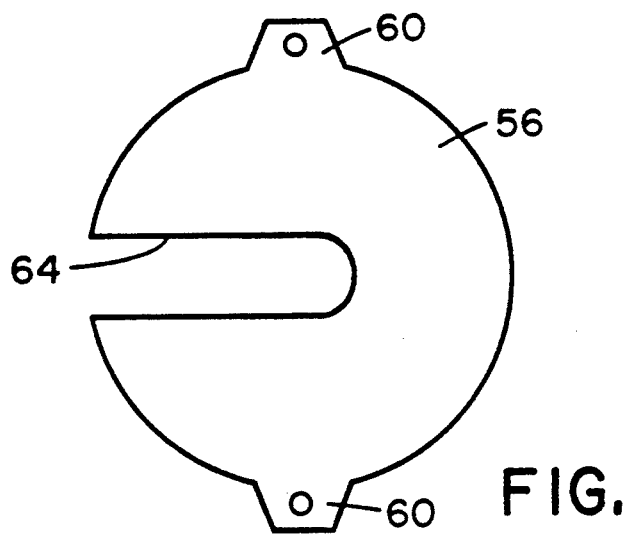
FIG. 7 is an enlarged front elevational view of a removable stop plate of the sample collecting apparatus of FIG. 1 after removal from the tubular housing.

Referring to FIGS. 1, 4 and 7, the sample collecting apparatus 10 also includes means in the form of a removable stop plate 56 mounted by fasteners 58 and matching tabs 60, 62 attached respectively on the stop plate 56 and the tubular housing 12 at the front open end 18 thereof. The stop plate 56 is engaged by the front end portion 34 of the sample container 14 so as to stop the sliding movement of the sample container 14 at the forward position in the tubular housing 12. The stop plate 56 is attached across the front open end 18 of the tubular housing 12 and has an elongated slot 64 defined therein. The arm 52 extends through the slot 64 in the stop plate 56.

The sample collecting apparatus 10 further includes a blocking element in the form of an annular collar 66. The annular collar 66 is mounted on the arm 52 adjacent to and spaced from the handle 54 at a distance calculated to bring the collar 66 into engagement with the stop plate 56 attached across the front open end 18 of the tubular housing 12 and thereby stop sliding movement of the sample container 14 at the rearward position. The fasteners 58 can be unfastened and the stop plate 56 removed in order to withdraw the sample container 14 from the tubular housing 12 for routine cleaning of the sample container 14 and tubular housing 12 of the sample collecting apparatus 10.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

Having thus described the invention, what is claimed is:

1. A sample collecting apparatus, comprising:
   (a) an elongated tubular housing having a hollow interior and a pair of spaced front and rear opposite open ends and a middle portion defining an opening in said housing located between and spaced from said opposite open ends;
   (b) a tubular sample container mounted within said housing for sliding movement along and rotational movement about a longitudinal axis extending between said opposite open ends of said housing, said container having spaced apart front and rear end portions and a middle portion located between said front and rear end portions, said container also having a pair of spaced walls disposed at opposite ends of said middle portion defining a sample holding cavity having an opening;
   (c) means for slidably and rotatably moving said container along and about said longitudinal axis between a rearward position in which said cavity of said container in a first orientation extends beyond said open rear end of said housing for receiving a sample and said forward end portion of said container substantially fills said open rear end of said housing and a forward position in which said cavity of said container in a second orientation aligns with said opening of said housing for discharging the sample and said rearward end portion of said container substantially blocks any path through said interior of said housing between said opening and said open rear end of said housing, said means for slidably and rotatably moving said container being an elongated arm connected to said front end portion of said container and extending forwardly therefrom through said housing and from said open front end thereof to where said arm has a portion that can be gripped to slidably move said container along and rotate said container about said longitudinal axis; and
   (d) means mounted at said open front end of said housing for allowing sliding and rotating movement of said elongated arm relative to and through said open front end of said housing and for engaging said front end portion of said container so as to prevent sliding movement of said container through said open front end of said housing and thereby stop said container at said forward position.

2. The apparatus of claim 1 wherein said portion of said arm is a transverse handle.

3. The apparatus of claim 1 wherein said sample container is angularly displaced approximately 180° upon being rotatably moved about said longitudinal axis between said first and second orientations.

4. The apparatus of claim 1 wherein:
   said front and rear end portions of said container have cylindrical shapes;
   said middle portion of said container have semi-cylindrical shaped defining said sample holding cavity with a semi-cylindrical shape; and
   said spaced end walls of said middle portion have circular shapes.

5. A sample collecting apparatus, comprising:
   (a) an elongated tubular housing having a hollow interior and a pair of spaced front and rear opposite ends and a middle portion defining an opening in said housing located between and spaced from said opposite ends, at least said rear end of said housing being open;
   (b) a tubular sample container mounted within said housing for sliding movement along and rotational movement about a longitudinal axis extending between said opposite ends of said housing, said container having spaced apart front and rear end portions and a middle portion located between said front and rear end portions, said container also having a pair of spaced walls disposed at opposite ends of said middle portion defining a sample holding cavity having an opening;
   (c) means for slidably and rotatably moving said container along and about said longitudinal axis between a rearward position in which said cavity of said container in a first orientation extends beyond said open rear end of said housing for receiving a sample and said forward end portion of said container substantially fills said open rear end of said housing and a forward position in which said cavity of said container in a second orientation aligns with said opening of said housing for discharging the sample and said rearward end portion of said container substantially blocks any path through said interior of said housing between said opening and said open rear end of said housing; and
   (d) means mounted at said front end of said housing for engaging said front end portion of said container to stop sliding movement of said container at said forward position, said front end of said housing being open, said engaging and stopping means being a removable stop plate attached across said open front end of said housing and having a slot defined therein.

6. The apparatus of claim 5 wherein said means for slidably and rotatably moving said container is an elongated arm connected to said front end portion of said container and extending forwardly therefrom through said housing and through said slot in said stop plate attached to said front end of said housing and extending from said housing to where said arm has a portion that can be gripped to slidably move said container along and rotate said container about said longitudinal axis.

7. The apparatus of claim 6 wherein said portion of said arm is a transverse handle.

8. The apparatus of claim 6 further comprising:

a blocking element mounted on said arm adjacent to said portion thereof for engaging said stop plate attached across said open front end of said housing to stop sliding movement of said container at said rearward position.

9. A sample collecting apparatus, comprising:
(a) an elongated cylindrical housing having a hollow interior and a pair of spaced front and rear opposite open ends and a semi-cylindrical middle portion defining a bottom opening in said housing located between and spaced from said opposite open ends;
(b) a tubular sample container mounted within said housing for sliding movement along and rotational movement about a longitudinal axis extending between said opposite open ends of said housing, said container having spaced apart front and rear end portions of cylindrical shapes and a middle portion of semi-cylindrical shape located between said front and rear end portions, said container also having a pair of spaced circular walls disposed at opposite ends of said middle portion defining a semi-cylindrical sample holding cavity having an opening; and
(c) means for slidably and rotatably moving said container along and about said longitudinal axis between a rearward position in which said cavity of said container in a generally upright orientation extends beyond said open rear end of said housing for receiving a sample and said forward end portion of said container substantially fills said open rear end of said housing and a forward position in which said cavity of said container in a generally inverted orientation aligns with said opening of said housing for discharging the sample and said rearward end portion of said container substantially blocks any path through said interior of said housing between said opening and said open rear end of said housing, said means for slidably and rotatably moving said container being an elongated arm connected to said front end portion of said container and extending forwardly therefrom through said housing and from said open front end thereof to where said arm has a portion that can be gripped to slidably move said container along and rotate said container about said longitudinal axis; and
(d) means mounted at said front end of said housing for allowing sliding and rotating movement of said elongated arm relative to and through said open front end of said housing and for engaging said front end portion of said container so as to prevent sliding movement of said container through said open front end of said housing and thereby stop said container at said forward position.

10. The apparatus of claim 9 wherein said portion of said arm is a transverse handle.

11. The apparatus of claim 9 wherein said container is angularly displaced approximately 180° upon being rotatably moved about said longitudinal axis between said first and second orientations.

12. A sample collecting apparatus, comprising:
(a) an elongated cylindrical housing having a hollow interior and a pair of spaced front and rear opposite open ends and a semi-cylindrical middle portion defining a bottom opening in said housing located between and spaced from said opposite open ends;
(b) a tubular sample container mounted within said housing for sliding movement along and rotational movement about a longitudinal axis extending between said opposite open ends of said housing, said container having spaced apart front and rear end portions of cylindrical shapes and a middle portion semi-cylindrical shape located between said front and rear end portions, said container also having a pair of spaced circular walls disposed at opposite ends of said middle portion defining a semi-cylindrical sample holding cavity having an opening;
(c) means for slidably and rotatably moving said container along and about said longitudinal axis between a rearward position in which said cavity of said container in a generally upright orientation extends beyond said open rear end of said housing for receiving a sample and said forward end portion of said container substantially fills said open rear end of said housing and a forward position in which said cavity of said container in a generally inverted orientation aligns with said opening of said housing for discharging the sample and said rearward end portion of said container substantially blocks any path through said interior of said housing between said opening and said open rear end of said housing; and
(d) means mounted at said open front end of said housing for engaging said front end portion of said container to stop sliding movement of said container at said forward position, said engaging and stopping means being a removable end wall attached across said open front end of said housing and having a slot defined therein.

13. The apparatus of claim 12 wherein said means for slidably and rotatably moving said container is an elongated arm connected to said front end portion of said container and extending forwardly therefrom through said housing and through said slot in said end wall attached to said open front end of said housing and extending from said housing to where said arm has a portion that can be gripped to slidably move said container along and rotate said container about said longitudinal axis.

14. The apparatus of claim 13 wherein said portion of said arm is a transverse handle.

15. The apparatus of claim 13 further comprising:
a blocking element mounted on said arm adjacent to said portion thereof for engaging said end wall attached across said open front end of said housing to stop sliding movement of said container at said rearward position.

16. A sample collecting apparatus, comprising:
(a) an elongated cylindrical housing having a hollow interior and a pair of spaced front and rear opposite open ends and a semi-cylindrical middle portion defining a bottom opening in said housing located between and spaced from said opposite open ends, said housing also having a bracket thereon for mounting said housing to a wall of an enclosure containing material to be sampled;
(b) a tubular sample container mounted within said housing for sliding movement along and rotational movement about a longitudinal axis extending between said opposite ends of said housing, said container having spaced apart front and rear end portions of cylindrical shapes and a middle portion of semi-cylindrical shape located between said front and rear end portions, said container also having a pair of spaced circular walls disposed at opposite ends of said middle portion defining a semi-cylindrical sample holding cavity having an opening;

(c) an elongated arm connected to said front end portion of said container and extending forwardly therefrom through said housing and from said open front end thereof, said arm having a handle thereon that can be gripped to slidably move said container along and rotate said container about said longitudinal axis between a rearward position in which said cavity of said container in an upright orientation extends beyond said open rear end of said housing for receiving a sample and said forward end portion of said container substantially fills said open rear end of said housing and a forward position in which said cavity of said container in an inverted orientation aligns with said bottom opening of said housing for discharging the sample and said rearward end portion of said container substantially blocks any path through said interior of said housing between said opening and said open rear end of said housing, said respective rearward and forward positions of said container being rotatably displaced approximately 180° from one another;

(d) a removable end wall attached across said open front end of said housing and having a slot defined therein receiving said arm therethrough, said end wall being engageable with said front end portion of said container to stop sliding movement of said container at said forward position; and (e) a collar mounted on said arm adjacent to said handle for engaging said end wall attached across said open front end of said housing to stop sliding movement of said container at said rearward position.

* * * * *